United States Patent [19]
Ishiguro et al.

[11] Patent Number: 6,030,115
[45] Date of Patent: Feb. 29, 2000

[54] METHOD OF MEASURING MELTING TEMPERATURE OF NUCLEIC ACID

[75] Inventors: Takahiko Ishiguro, Yokohama; Juichi Saitoh, Yamato, both of Japan

[73] Assignee: Tosoh Corporation, Japan

[21] Appl. No.: 09/088,728

[22] Filed: Jun. 2, 1998

[30] Foreign Application Priority Data

Jun. 5, 1997 [JP] Japan .................................. 9-147825

[51] Int. Cl.[7] ........................... G01N 25/04; G01N 1/00; G12Q 1/68
[52] U.S. Cl. ................. 374/16; 374/17; 436/94; 436/47; 436/172; 435/6
[58] Field of Search .................. 374/16, 17; 436/94, 436/47, 172; 435/6

[56] References Cited

U.S. PATENT DOCUMENTS

| | | | |
|---|---|---|---|
| 4,544,546 | 10/1985 | Wang et al. | 436/94 |
| 5,356,776 | 10/1994 | Kambara et al. | 436/94 |
| 5,683,657 | 11/1997 | Mian | 436/94 |
| 5,686,244 | 11/1997 | Gudibande et al. | 436/94 |

*Primary Examiner*—G. Bradley Bennett
*Assistant Examiner*—Gail Verbitsky
*Attorney, Agent, or Firm*—Nixon & Vanderhye

[57] ABSTRACT

A method of measuring a melting temperature of a nucleic acid, which comprises a step of monitoring the fluorescent intensity of a mixture of a sample and a probe which is labeled with a fluorescent intercalative dye and contains a base sequence complementary to a specific nucleic acid in the sample, while varying the temperature of the mixture.

8 Claims, 7 Drawing Sheets

TEMPERATURE DEPENDENCE OF RELATIVE FLUORESCENCE INTENSITY

TEMPERATURE DEPENDENCE OF RELATIVE
FLUORESCENCE INTENSITY

RELATIVE FLUORESCENCE INTENSITY AFTER
SUBTRACTION OF THE BACKGROUND FLUORESCENCE

TEMPERATURE DEPENDENCE OF FLUORESCENCE
INTENSITY (DIFFERENCE IN TEMPERATURE
DEPENDENCE DUE TO POINT MUTATION)

Tm MEASUREMENT USING FLUORESCENT PROVE
(DIFFERENCE IN Tm DUE TO POINT MUTATION)

DETECTION OF POINT MUTATIONS IN
HCV RNA IN SERUM SAMPLES

METHOD OF MEASURING MELTING TEMPERATURE OF NUCLEIC ACID

The present invention relates to a method of assay of a specific nucleic acid anticipated in a gene mixture containing DNA or RNA, and is useful for gene diagnosis in the field of clinical diagnosis, for exploring unknown genes. The method of the present invention is particularly useful as a method of evaluating the homology of an unknown gene with a control gene sequence and as a method of detecting genetic mutations.

It is known that the stability of nucleic acids forming complementary base pairs sensitively depends on temperature. The temperature dependence makes it possible to evaluate the homology of an unknown gene to a control gene in nucleic acid sequence by measuring the melting temperature (Tm) of a nucleic acid. For example, in molecular phylogeny and bacteriology, because long nucleic acid sequences from sample organisms which are virtually difficult to determine are dealt with from the necessity of gene identification, an unknown nucleic acid is examined on its homology with a known nucleic acid sequence by measuring the melting point of their hybrid in solution. On the other hand, since some hereditary diseases are known to be attributed to point mutations in specific nucleic acid sequences, mutations in such nucleic acid sequences have been detected by comparing the melting temperature of the hybrid of a nucleic acid in a sample to be examined and an oligomer (a nucleic acid probe) complementary to the specific nucleic acid with the melting temperature measured by using a control nucleic acid containing no mutations.

For measurement of Tm, the hyperchromicity of nucleic acids has been usually utilized. Nucleic acids show spectroscopic absorption at a wavelength of 260 nm, and the absorbance decreases as single strands of nucleic acids form double helices. When the absorbance of a nucleic acid sample is measured while the temperature is varied, and plotted against the temperature, Tm is defined as the inflection point of the resulting sigmoid curve.

Tm is known to depend on the length of the sequence of a nucleic acid forming complementary base pairs (n), the G and C content in the sequence, the concentrations of salt ($\mu$) and the denaturing agent (% FA) in the sample solution, and, in general, follows an empirical equation $TM=81.5+16.6 \log(\mu)+0.41 (\% GC)-500/n-0.61 (\% FA)$.

However, absorbance measurement is not available for determination of Tm in the case of samples containing relatively small amounts of nucleic acids. For one thing, Lambert-Beer's law limits the measurable absorbance range to 2.00 D or below. On the other hand, usual measuring instruments have their performance limitations in terms of sensitivity around 0.10 D. This means that the measurable nucleic acid concentration range is about from 3 to 10 $\mu$g/ml.

The recent development of the polymerase chain reaction has made possible in vitro amplification of a specific region of a specific nucleic acid in a sample. Therefore, it is possible to amplify a specific region of a specific nucleic acid in a sample by PCR for absorbance measurement. However, tens of copies of a nucleic acid is amplified only to several ng, which is not sufficient for the above-mentioned method based on the absorbance measurement.

Further, detailed thermodynamic studies revealed dependence of the Tm of a nucleic acid on its concentration (Breslauer et al, Proc. Nat. Acad. Sci. 83, 3746–50, 1986). Breslauer et al. reported that the melting temperatures of the sequence, atgcatgcatgcatgcatgc, in the presence of 50 mM of a salt were 67.5, 63.5° C., 59.5° C. and 55.6° C. at nucleic acid concentrations of 50 nM, 5 nM, 0.5 nM and 0.05 nM, respectively.

This indicates the necessity for a more sensitive method of measuring Tm.

For example, it is known that use of a fluorescent intercalative dye which emits enhanced fluorescence on binding to a double-stranded nucleic acid can afford a sensitive method of measuring Tm even if nucleic acid concentrations of samples are low. In this method, the fluorescence intensity of a sample solution containing a probe and an intercalative dye added thereto is monitored while the temperature of the solution is varied. At high temperatures, single strands of a nucleic acid are liberated, and as the temperature of the solution is lowered, formation of the hybrid of the nucleic acid and the probe accompanied by increase in fluorescence intensity is observed.

However, in this method, when the fluorescence intensity is monitored while the sample solution is cooled down, the intercalator binds to double helices of other nucleic acids in the sample solution, double strands of the target nucleic acid formed by re-association of complementary single strands which originally formed double strands at room temperature, or intramolecular double helices formed by folding of a single-stranded target nucleic acid, and the consequential background fluorescence obstructs accurate measurement of the melting temperature of the hybrid of the target nucleic acid and the probe.

Alternatively, by application of dot hybridization to measurement of melting temperature is attempted using adsorb nucleic acid-absorptive membranes. Commercially available membranes which can easily adsorb and immobilize nucleic acids are spotted with a solution containing a hybrid between a target nucleic acid and a probe labeled with a fluorescent dye or an isotope and dried. The membranes are soaked in a buffer having a predetermined salt concentration while the temperature of the buffer is varied, and at certain temperatures, the membranes are taken out, and the fluorescence intensity or the radioactivity of the label remaining on the membranes is measured.

However, the above-mentioned method involves cumbersome operations and requires skill to yield reliable results. For example, for more reliable results, several membranes spotted with a hybrid are soaked in buffers maintained at predetermined temperatures for a given period of time and then subjected to measurement of the fluorescence intensity or the radioactivity. However, use of several membranes increases operational complexity and labor and therefore produces a new problem in actual clinical situations in which a great number of samples have to be examined.

Further, for hybridization of a probe and a target nucleic acid, a heating step (denaturing) for melting double strands of DNA into single strands after addition of a probe to a reaction solution and a subsequent cooling step (annealing) for forming a double-stranded DNA from the probe DNA and the target DNA are virtually essential. Besides, at the time of determination of the hybridization conditions and analysis of the results, the possibility of liberation of the hybrid from membranes during incubation of the membranes must be considered fully.

On the other hand, the present inventors developed a fluorescent intercalative dye-labeled probe which can recognize a specific nucleic acid sequence by linking a fluorescent intercalative dye as a label to a single-stranded oligonucleotide complementary in nucleic acid sequence to a specific nucleic acid sequence of the specific nucleic acid, so that when the single-stranded oligonucleotide hybridizes with the specific nucleic acid, the intercalative dye intercalates into the resulting double-stranded oligonucleotide to alter the florescent property (Japanese Patent Application JP7-185599, EP-A-714986, and Nucleic Acids Research 24(24), 4992–4997 (1996)). Use of the fluorescent intercalative dye-labeled probe for detecting unknown sequences enables detection and quantification of the resulting hybrid without separating the unhybridized probe, because the fluorescent intercalative dye as the label alters fluorescent property upon hybridization of the probe with the specific nucleic acid. Therefore, the probe can be applied to assay of a specific nucleic acid in a sample by way of measurement of the melting temperature.

The present invention has been accomplished from the above-mentioned standpoint and relates to a method of assay of a specific nucleic acid sequence in a gene mixture containing DNA or RNA. The object of the present invention is to provide a simple and accurate one-step method of measurement of the melting temperature (Tm) of a nucleic acid homogeneous useful for gene diagnosis in the field of clinical diagnosis and for exploring unknown genes, a method of evaluating the homology of an unknown gene with a control gene in base sequence and a method of detecting mutations in genes.

To attain the above-mentioned object, the present invention provides a method of measuring a melting temperature of a nucleic acid, which comprises a step of monitoring the fluorescent intensity of a mixture of a sample and a probe which is labeled with a fluorescent intercalative dye and contains a base sequence complementary to a specific nucleic acid in the sample, while varying the temperature of the mixture, on the basis that the fluorescent intercalative dye as the label intercalates into a double-stranded oligonucleotide in the hybrid of the specific nucleic acid and the probe and alters its fluorescence.

According to the present invention, since the fluorescence intensity of the fluorescent intercalative dye increases upon formation of the hybrid between the probe and the target nucleic acid, it is possible to detect and quantify the hybrid without separating the excessive unhybridized probe, and monitoring of the fluorescence intensity of the mixture while the temperature of the mixture is varied, enables homogeneous simple one-step measurement of the melting temperature of a specific nucleic acid.

Therefore, according to the present invention, even if other double-stranded nucleic acids coexist in the sample, even if complementary single strands which originally formed double strands at room temperature re-form double strands or even if a single-stranded nucleic acid forms an intramolecular double helices by folding, since the intercalator-labeled probe specifically recognizes the specific sequence of the target nucleic acid and hybridized with the target nucleic acid to increase the fluorescence intensity, it is possible to obviate the problem attributable to the background fluorescence which arises when the melting temperature is measured by monitoring the fluorescence intensity of a sample solution containing a probe and an intercalative dye while varying temperature.

Further, measurement of the melting temperature of the hybrid of a target nucleic acid in a sample and an intercalator-labeled probe complementary in sequence to a specific nucleic acid sequence in the specific nucleic acid makes it possible to detect mutations in the specific nucleic acid sequence by comparing the melting point with the melting point of a hybrid with a nucleic acid containing no mutations. Further, once the melting temperature of a hybrid with a nucleic acid containing no mutations is determined, simple one step detection of mutations by comparing the fluorescence intensity of a sample solution containing an intercalator-labeled probe around the melting temperature with the fluorescence intensity measured with a nucleic acid containing no mutation is possible. For example, the present invention provides means which is clinically effective in planning of therapy for hepatitis C virus, which is classified according to RNA sequence into several types which respond differently to the therapeutic action of interferon.

Further, the method of measuring Tm by fluorescent detection of hybrids according to the present invention is generally more effective than the method based on the hyperchromicity for relatively small amounts of nucleic acids in samples and is also applicable to samples containing only tens of copies of target nucleic acids, which can be amplified to only several ng even by PCR.

In addition, since the present invention permits homogeneous assay without separation of the excessive unhybridized probe, the method of the present invention does not require operations involved in measurement of Tm by dot hybridization using nucleic acid-absorptive membranes, such as spotting of membranes with hybrids, incubation of membranes in buffers and subsequent washing of membranes, and is simpler and labor-saving. Especially, the method of the present invention can be used in actual clinical situations in which a lot of samples have to be examined in a short time.

Figure 1:
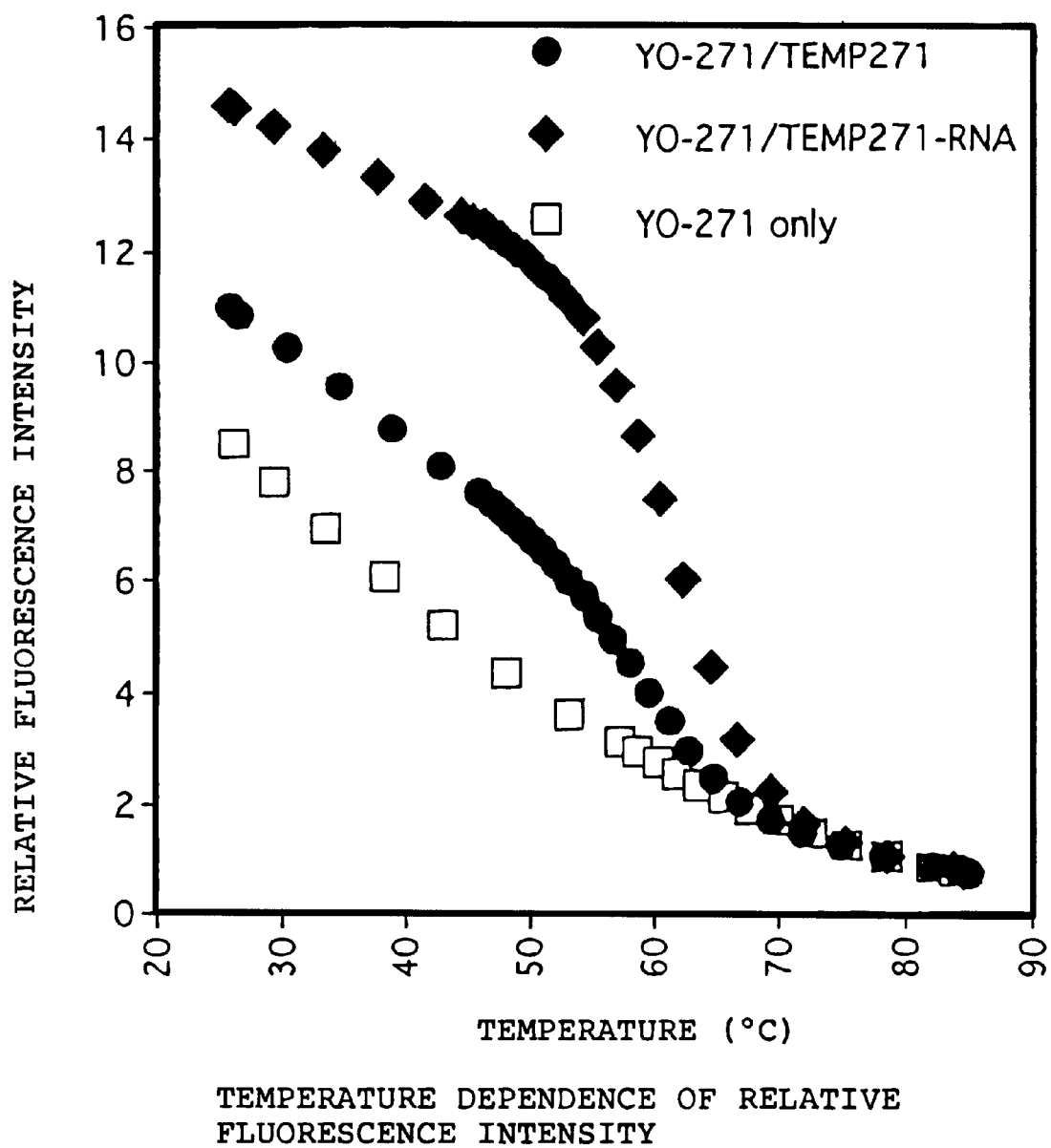
FIG. 1 shows the temperature dependence of the fluorescence intensities of a probe and mixtures of the probe and target nucleic acids.

Now, the present invention will be described in further details.

The probe used in the present invention is an oligonucleotide which is complementary in sequence to the target nucleic acid and is labeled with a fluorescent intercalative dye which alters its fluorescence on intercalation into double-stranded DNA (Japanese Patent Application JP7-185599, EP-A-714986, Nucleic Acid Research, 24(24), 4992–4997(1996)). The fluorescent intercalative dye is not particularly limited, as long as it alters the fluorescence on intercalation into double-stranded DNA. However, those which emits enhanced fluorescence on intercalation are preferable in view of the easiness of monitoring, and particularly, thiazole orange, oxazole yellow and their derivatives are preferable because they shows radical alternation in the fluorescence.

The fluorescent intercalative dye is covalently bonded to the oligonucleotide, if necessary, via a linker with an appropriate length. Although any linkers that do not hinder the fluorescent intercalative dye from intercalating into double-stranded DNA may be used, difunctional hydrocarbons having functional groups at both ends are preferred because they are easy to bond to oligonucleotides. Further, for example, a commercial kit (C6-Thiolmodifier, Clontech) may be used. The fluorescent intercalative dye as the label may be bonded to any sites of the oligonucleotide, including the 5'- end, the 3'- end and the center, as long as it neither hinders the fluorescent intercalative dye from intercalating into double-stranded DNA nor hinders the oligonucleotide from hybridizing with the target nucleic acid. The region of the probe which is complimentary to the target nucleic acid is preferably from 6 to 100 nucleotides, more preferably from 10 to 30 nucleotides long in order to secure the specificity for the target nucleic acid.

In the present invention, a commercial fluorometer can be used for measuring the fluorescence of reaction solutions, as long as it excites the intercalator in a reaction solution at a wavelength at which the intercalator shows an absorption peak and measures the intensity of the fluorescence emitted from the intercalator. The fluorescence can be monitored while the temperature of a reaction solution is continuously varied, for example by loading a reaction solution preincubated at a temperature well higher than the melting temperature into a fluorometer maintained at room temperature and measuring the temperature and the fluorescence intensity simultaneously while the reaction solution gradually cools down to room temperature. For monitoring of the temperature of a reaction solution, any means which can measure the temperature of a reaction solution in a fluorometer may be employed. For this purpose, devices which have remote thermosensitive microterminals and record temperature change converted into electrical signals, such as thermocouples may be employed. Of course, a fluorometer equipped with a thermostat which can maintain a reaction solution at a desired temperature may be employed.

Figure 7:
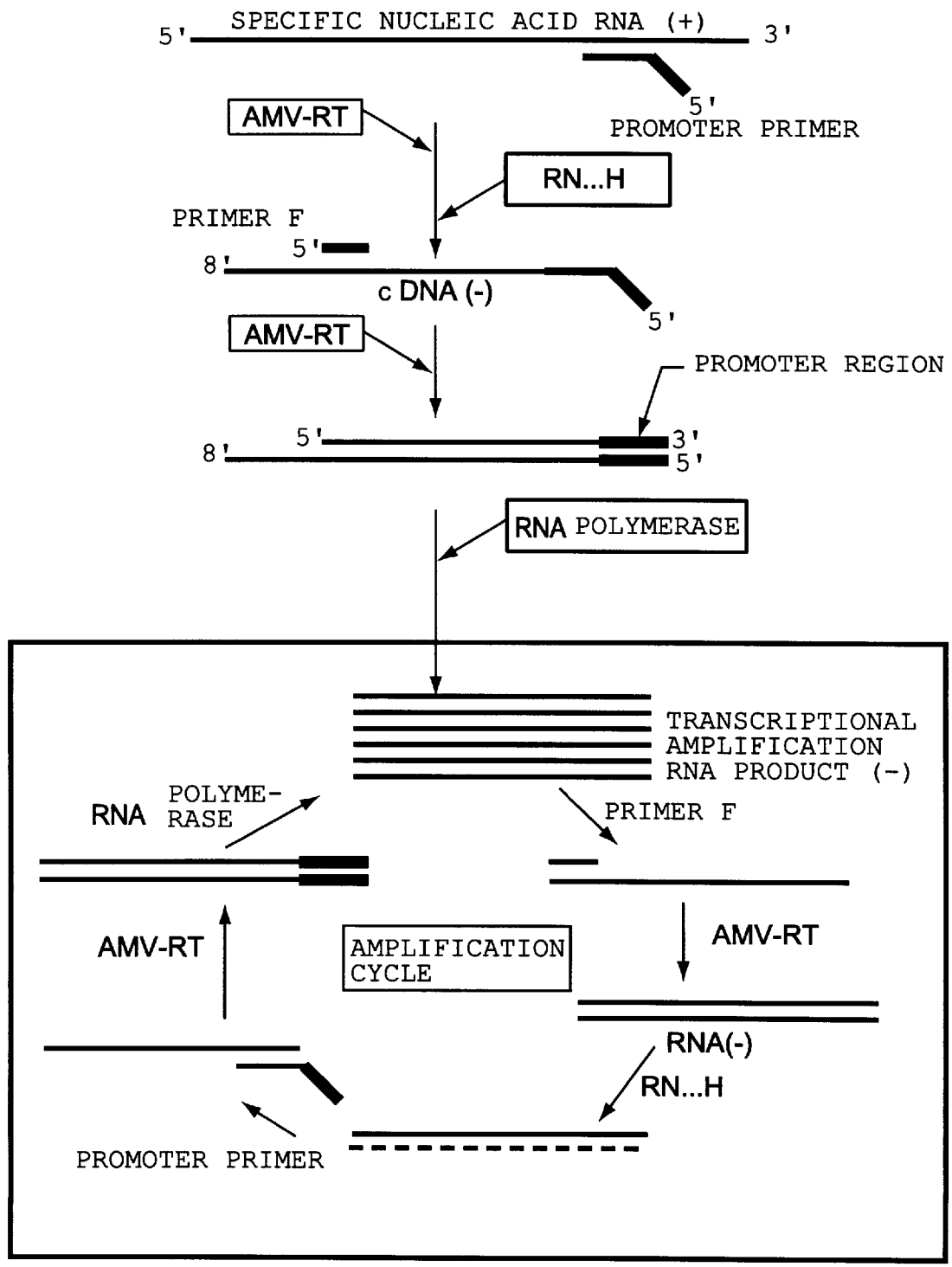
FIG. 7 shows an outline of amplification of nucleic acids by the NASBA method.

It is anticipated that the above-mentioned sample contains the target specific nucleic acid, and in the present invention, the specific nucleic acid in a sample may be amplified beforehand. The method of amplifying the specific nucleic acid is not particularly limited, but for example, the polymerase chain reaction (PCR) method, the NASBA method (Journal of Virological Methods, 43, 177–188, 1993) and the amplification method disclosed in Japanese Patent Application JP9-10996 are particularly preferred. Amplification by the NASBA method will be outlined by reference to FIG. 7. A sample is mixed with a solution containing two primers specific for the target nucleic acid and three enzymes, AMV reverse transcriptase, RNaseH and RNA polymerase and incubated at a constant temperature so that the enzymes act cooperatively to exponentially amplify an RNA having a sequence complementary to the target nucleic acid. One of the two primers specific for the target nucleic acid has a promoter sequence for the RNA polymerase upstream and a downstream sequence complementary to the specific nucleic acid. The RNA thus produced may be subjected to the method of the present invention. Ordinary reagents used for PCR such as DNA polymerase may be used in amplification of the specific nucleic acid by PCR.

Now, the present invention will be described in further detail, but it should be understood that the present invention is by no means restricted to these specific Examples.

EXAMPLE 1

The melting temperatures (Tm) of target DNA and RNA were measured by the method of the present invention.
1) 140 μl of reaction solutions containing (1) a fluorescent intercalative dye-labeled probe (YO-271) only, (2) YO-271 and the target DNA (TEMP271) and (3) YO-271 and the target RNA (TEMP271-RNA) were loaded into fluorometric cuvettes. The materials used and the compositions of the reaction solutions are described below.
(Fluorescent intercalative dye-labeled probe) YO-271:5'-CTGGC*GGGGGCTG-3';
* indicates the site labeled with oxazole yellow (YO)
(Target DNA)
TEMP271: 5'-GTGCCCCCGCGAG-3';
containing the base sequence 221 to 233 of HCV cDNA (the base numbers should be referred to Kato et al. (Kato, N., Hijikata, M., Ootsuyama, Y., et al. (1990) Proc. Natl. Acad. Sci USA, 87, 9524–9528)). The sequence of bases Nos. 3 to 13 is complementary to YO-271.
(Target RNA)
TEMP271-RNA: 5'-GUGCCCCCGCGAG-3'
(Composition of the reaction solutions)
×1 mM SSC
1 mM EDTA
50 nM YO-271
50 nM TEMP271 or TEMP271-RNA
2) 150 μl of mineral oil was added to the reaction solutions.
3) While the temperatures of the reaction solutions in the fluormetric cuvettes were monitored, the reaction solutions were gradually cooled from about 84° C. to about 26° C. At the same time, the fluorescence intensities were measured at an excitation wavelength of 490 nm and an emission wavelength of 510 nm.

Figure 2:
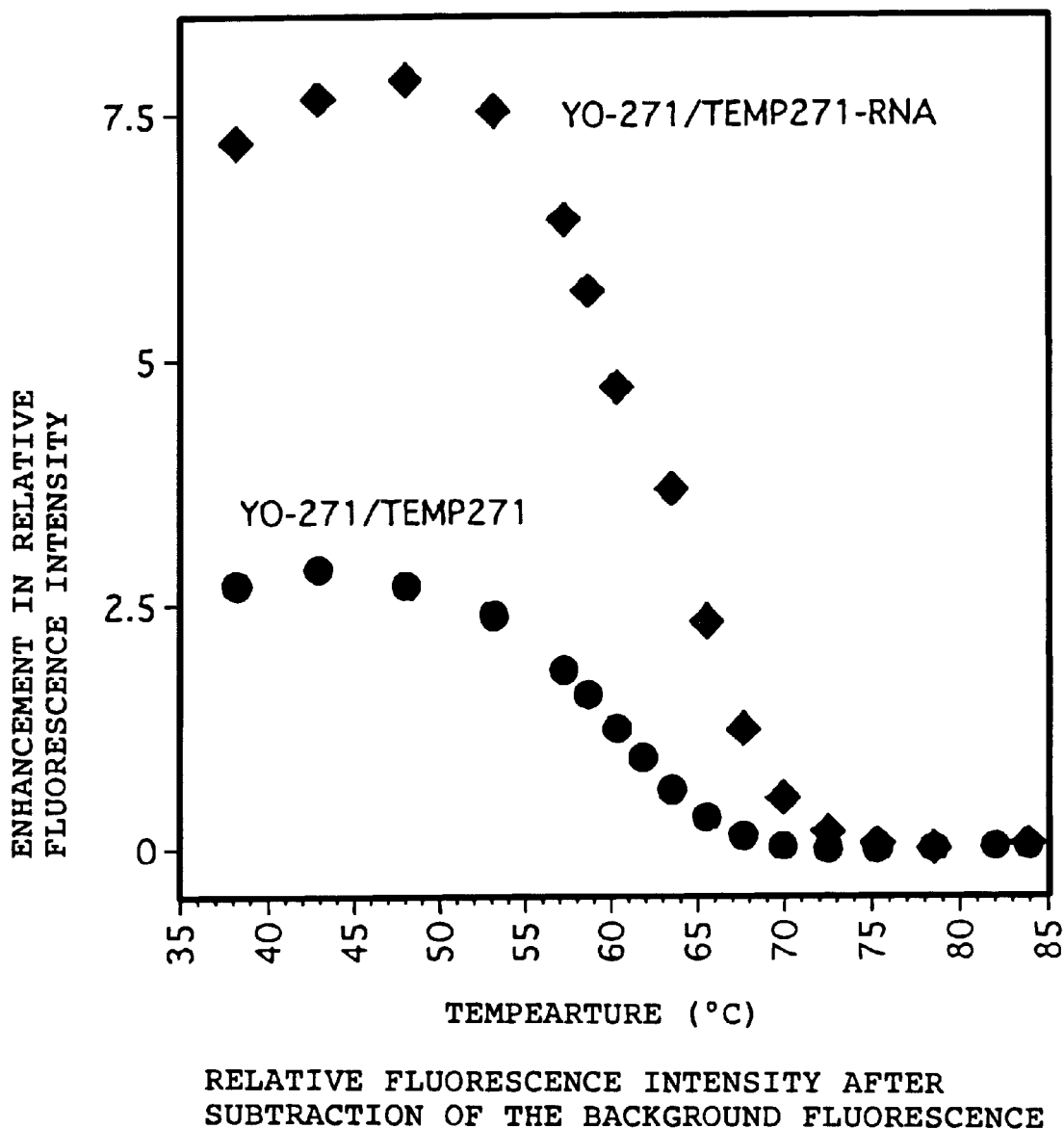
FIG. 2 shows melting curves of the hybrids between the probe and the target nucleic acids obtained by subtracting the fluorescence intensity of the probe from the measured fluorescence intensities of the hybrids shown in FIG. 1.

The relative fluorescence profiles for (1), (2) and (3) in relation to the fluorescence intensities at 80° C. are shown in FIG. 1. The relative fluorescence profiles after subtraction of the relative fluorescence intensity for the reaction solution containing YO-271 only are shown in FIG. 2. The Tm values determined from FIG. 2 (the results of the fluorescent Tm measurement) are shown in Table 1.

TABLE 1

| Probe/target | Tm value (° C.) |
| --- | --- |
| YO-271/TEMP271 | 59 |
| YO-271/TEMP271-RNA | 62 |

The results are consistent with a previous report that a DNA-RNA double strand has a higher Tm than a DNA-DNA double strand. It was possible to measure Tm at probe and target nucleic acid concentrations as low as 50 nM (30 times as low as the concentrations required for absorbance measurement at 260 nm).

This proves that the present invention enables sequence specific detection of a specific nucleic acid with a high sensitivity.

EXAMPLE 2

The Tm's of target RNAs containing point mutations were determined by the fluorescence measurement using a fluorescent intercalative dye-labeled probe according to the present invention.
1) 40 μl of reaction solutions containing (1) a probe (YO-271) only, (2) YO-271 and a target RNA (Type II-RNA) and (3) YO-271 and a target RNA (Type III-RNA) were loaded into fluorometric cuvettes. The materials used and the compositions of the reaction solutions are described below (target DNA).
TypeII-RNA: 5'-GUGCCCCCGCGAG-3', containing the base sequence 221 to 233 of HCV (Kato et al.) The sequence of bases Nos. 3 to 13 is complementary to YO-271.
(Target RNA)
TypeIII-RNA: 5'-GUGCCCCCGCAAG-3', corresponding to Type II-RNA in which the 11th G is replaced by A.

(Composition of the reaction solutions)
40 mM Tris.HCl, pH8.0
25 mM KCl
4 mM MgCl2
50 nm YO-271
50 nM Type II-RNA or Type III-RNA
2) 150 μl of mineral oil was added to the fluorometric cuvettes.
3) While the temperatures of the reaction solutions in the fluormetric cuvettes were monitored, the reaction solutions were gradually cooled from about 85° C. to about 26° C. At the same time, the fluorescence intensities were measured at an excitation wavelength of 490 nm and an emission wavelength of 510 nm.

Figure 3:
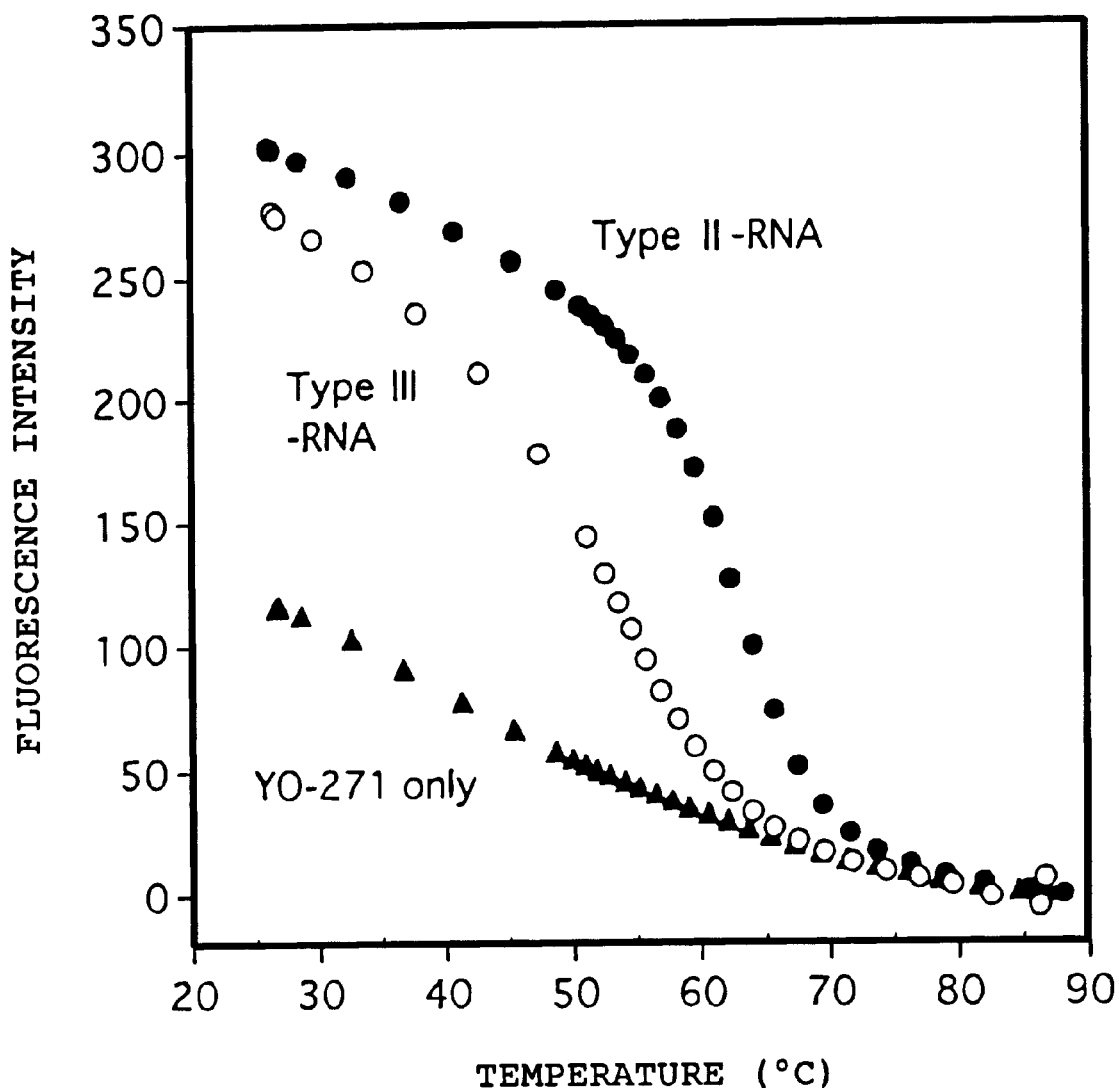
FIG. 3 shows temperature dependence of the fluorescence intensities of the probe only and mixtures of the probe and target nucleic acids.
Figure 4:
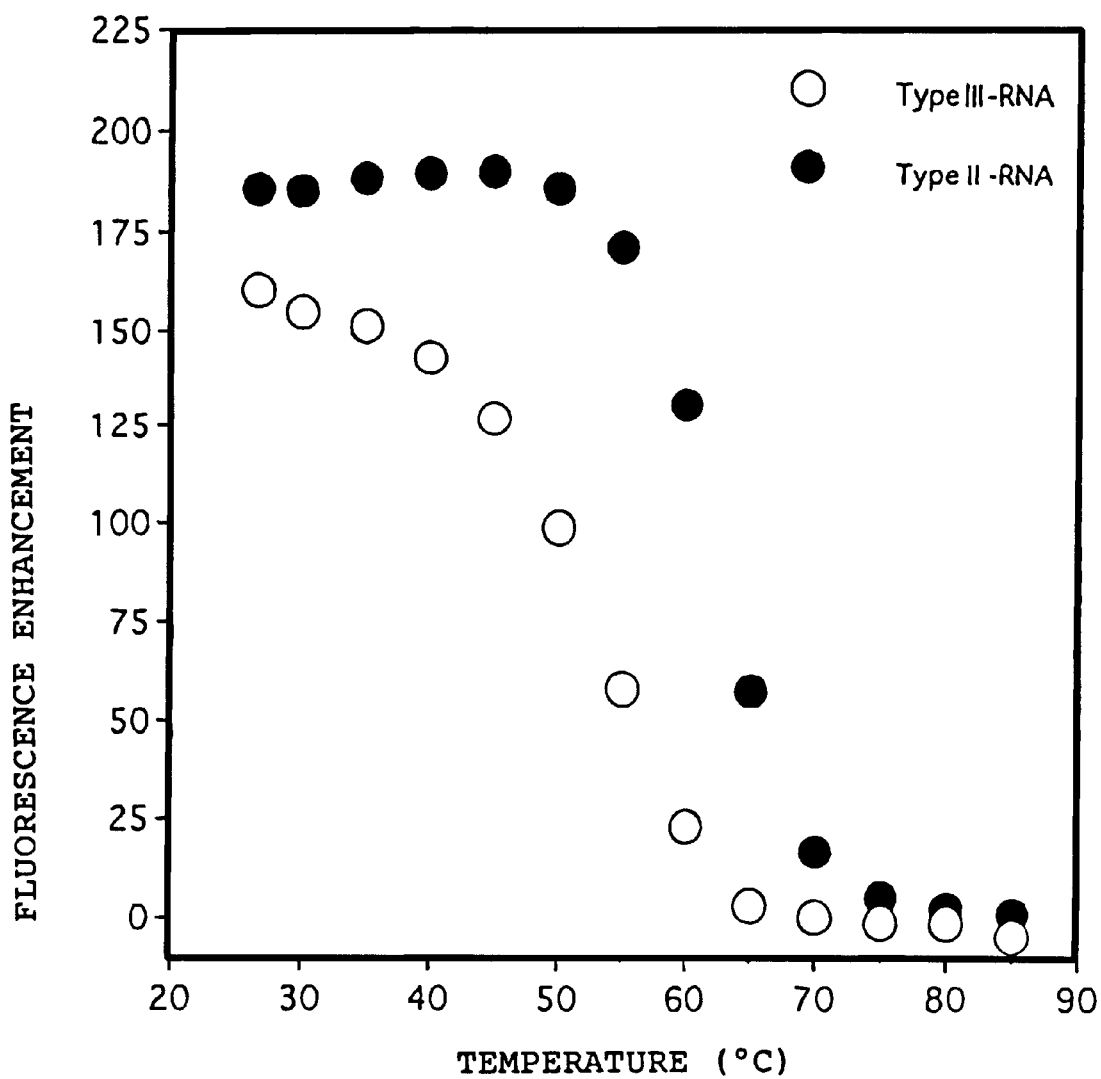
FIG. 4 shows melting curves of the hybrids of the probe and the target nucleic acids after subtraction of the fluorescence intensity of the probe only shown in Table 3.

The relative fluorescence profiles for (1), (2) and (3) in relation to the fluorescence intensities at 80° C. are shown in FIG. 3. The relative fluorescence profiles after subtraction of the relative fluorescence intensity for the reaction solution containing YO-271 only are shown in FIG. 4. The Tm values determined from FIG. 4 (the results of the fluorescent Tm measurement) are shown in Table 2.

TABLE 2

| Probe/target | Tm value (° C.) |
|---|---|
| YO-271/TypeII-RNA | 63 |
| YO-271/TypeIII-RNA | 53 |

Thus the Tm values for Type II-RNA and Type II-RNA were different by 10° C. This proves that the present invention enables homogeneous detection of one base substitutions in a specific nucleic acid with a high sensitivity.

EXAMPLE 3

The method of the present invention was applied to detection of point mutations.
1) 140 μl of reaction solutions containing (1) a fluorescent intercalative dye-labeled probe (YO-271) only, (2) YO-271 and a target DNA (each of TEMP271 and target DNAs 3 to 13) were loaded into fluorometric cuvettes. The materials used and the compositions of the reaction solutions are described below.
(Target DNAs)
The target DNAs contained the sequence of bases Nos. 221 to 233 of HCV cDNA (Kato et al.), and the sequence of bases Nos. 3 to 13 of each DNA is complementary to YO-271.

TEMP271: 5'-GTGCCCCCGCGAG-3'
DNA 3: 5'-GTACCCCCGCGAG-3'
DNA 4: 5'-GTGACCCCGCGAG-3'
DNA 5: 5'-GTGCACCCGCGAG-3'
DNA 6: 5'-GTGCCACCGCGAG-3'
DNA 7: 5'-GTGCCCACGCGAG-3'
DNA 8: 5'-GTGCCCCAGCGAG-3'
DNA 9: 5'-GTGCCCCCACGAG-3'
DNA 10: 5'-GTGCCCCCGAGAG-3'
DNA 11: 5'-GTGCCCCCGCAAG-3'
DNA 12: 5'-GTGCCCCCGCGTG-3'
DNA 13: 5'-GTGCCCCCGCGAA-3'
(Composition of the reaction solutions)
10 mM Tris.HCl, pH8.3
50 mM KCl
50 nM YO-271
50 nM TEMP271 or one of the target DNAs 3–13

2) The fluorescence intensities at cuvettes temperatures of 37° C. and 51° C. were measured at an excitation wavelength of 490 nm and an emission wavelength of 510 nm.

Figure 5:
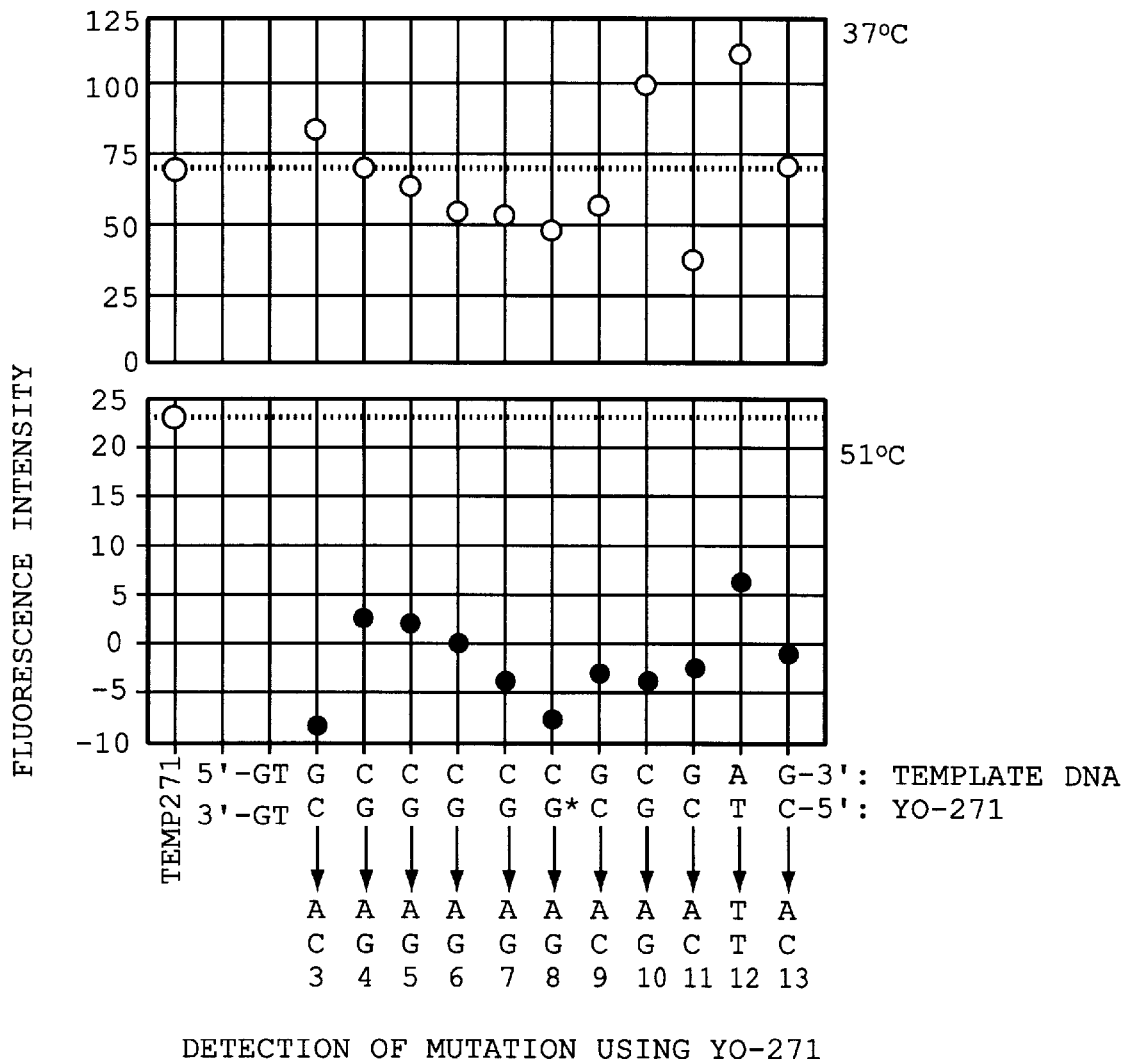
FIG. 5 shows the relationship between the fluorescence intensities at 37° C. and 51° C. and the positions of mutations.

The fluorescence intensities with (1) and (2) at 37° C. and 51° C. were measured, and are shown in FIG. 5 after subtraction of the fluorescence intensities with YO-271 only. The fluorescence intensities at 37° C. differed depending on the positions of the mutations, and the lowest fluorescence intensity was obtained with DNA 11. In contrast, there was not appreciable increase in fluorescence intensity at 51° C. except for complementary TEMP271.

This proves that the present invention enables not only detection but also location of one base substitutions.

EXAMPLE 4

Measurement of the melting temperature of the hybrid of a target nucleic acid in a sample and an intercalator-labeled probe complementary in sequence to a specific nucleic acid sequence in the specific nucleic acid makes it possible to detect mutations in the specific nucleic acid sequence by comparing the melting point with the melting point of a hybrid with a nucleic acid containing no mutations. Further, once the melting temperature of a hybrid with a nucleic acid containing no mutations is determined, simple one step detection of mutations by comparing the fluorescence intensity of a sample solution containing an intercalator-labeled probe around the melting temperature with the fluorescence intensity measured with a nucleic acid containing no mutation is possible.

From this viewpoint, homogeneous fluorescent detection of point mutations in HCV RNA in serum samples from patients with chronic hepatitis C, comprising fine Type III (Okamoto et al.) HCV-infected sera, three sera infected with both Type II and Type III HCVs and three Type II HCV-infected sera, was attempted using a probe containing a sequence complementary to Type II HCV RNA by the method according to claim 7 of the present invention.
1) Nucleic acids were extracted from 200 μl of each serum sample by using a commercial nucleic acid extraction kit using an organic solvent and a protein denaturing agent (Tosoh Corp.).
2) Each of the extracted RNA pellets were dissolved in 40 μl of a sample diluent, and a 10 μl portion of the resulting solution was subjected to fluorescent measurement as a sample.
(Composition of the sample diluent)
10 mM Tris.HCl (pH8.0)
0.1 mM EDTA
100 μg/ml yeast RNA
1 mM DTT
2 U/μl RNase Inhibitor
3) 5 μl of an RT solution was dispensed into each PCR tube, and 10 μl of each sample or distilled water for injection as the negative control was added.
(Composition of the RT solution)
30 mM Tris.HCl (pH8.3)
150 mM KCl
13.6 mM MgCl12
4.3 mM dNTPs
3 mM ETT
3 U/μl RNase inhibitor
6 U/μl MMLV reverse transcriptase
3.6 μM primer R: 5'-GCACTCGCAAGCACCCTATCA-3'
4) Reverse transcription was carried out a thermal cycler.
(Reverse transcription conditions)
42° C. 10 minutes
99° C. 6 minutes 5) 60 μl of a PCR solution was added.
(Composition of the PCR solution)
10 mM Tris.HCl (pH8.3)
50 mM KCl
1.6 mM MgCl2
0.025% nonidet P40
37.5 U/ml Taq DNA polymerase for hot start
0.3 μM promoter primer: 5'- ATTTAGGTGACACTATA-GAATACAACACTCCA CCATAGATCACTCCCCTG-3'
6) PCR was carried out in a thermal cycler.
(PCR conditions)
 1) 95° C. 9 minutes
 Then, the cycle comprising the following 2) to 4) was repeated 40 times.
 2) 95° C. 30 seconds
 3) 67° C. 30 seconds
 4) 72° C. 1 minute
7) 70 μl of each of the PCR products and 65.3 μl of a transcription solution were mixed.
(Composition of the transcription solution)
75.3 mM Tris.HCl (pH8.0)
15.1 mM MgCl2
10.7 mM DTT
0.86 mM NTPs
4.3 mM spermidine
2.2 U/μl RNase Inhibitor
53.6 nM YO-271
8) 4.7 μl of SP6 RNA polymerase (30 U/μl) was added.
9) The resulting reaction mixtures were allowed to react at 37° C. for 30 minutes.
10) To the resulting transcription products, 2.8 μl of 0.5 M EDTA was added.
11) Each of the transcription products was loaded into a fluorometric cuvette maintained at 60° C. in a fluorometer and the fluorescence intensity was measured at an excitation wavelength of 490 nm and an emission wavelength of 510 nm.

Figure 6:
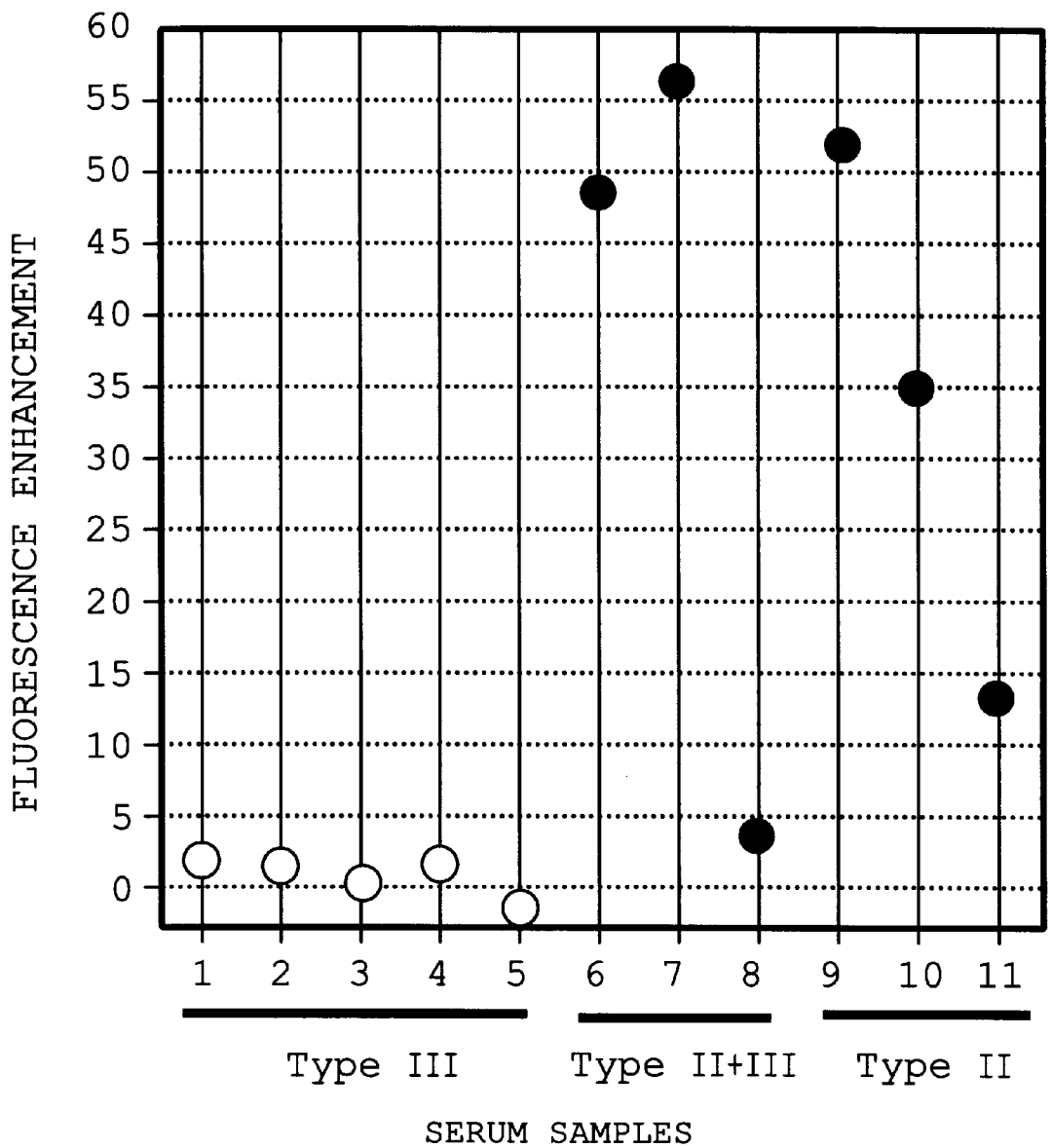
FIG. 6 shows the results of fluorescence measurement of clinical samples at 65° C.

FIG. 6 shows fluorescence enhancements at 65° C. based on the fluorescence intensity of the negative control. The fluorescence enhancements of Type II sera were significant as compared with those of Type III sera. All the multiple infected sera containing both Type II and Type III RNAs showed great fluorescence enhancements except one which is assumed to contain a trace of Type II HCV RNA.

From the above results, it can be concluded that use of the fluorescent probe complementary to Type II HCV RNA enables homogeneous detection of Type II HCV RNA. This proves that an intercalator-labeled probe makes it possible to detect mutations in nucleic acid samples by differential fluorescence measurement around its melting temperature against a nucleic acid containing no mutation.

As described above, according to the present invention, since the fluorescence intensity of the fluorescent intercalative dye increases upon formation of the hybrid between the probe and the target nucleic acid, it is possible to detect and quantify the hybrid without separating the excessive unhybridized probe, and monitoring of the fluorescence intensity of the mixture while the temperature of the mixture is varied, enables homogeneous simple one step measurement of the melting temperature of a specific nucleic acid.

Therefore, according to the present invention, since the intercalator-labeled probe specifically recognizes the specific sequence of the target nucleic acid and hybridized with the target nucleic acid to increase the fluorescence intensity, it is possible to measure the melting temperature of the target nucleic acid without increase in the background fluorescence attributable to other double-stranded nucleic acids coexisting in the sample, or an intramolecular double helices in a single-stranded nucleic acid.

Further, measurement of the melting temperature of the hybrid of a target nucleic acid in a sample and an intercalator-labeled probe complementary in sequence to a specific nucleic acid sequence in the specific nucleic acid makes it possible to detect mutations in the specific nucleic acid sequence by comparing the melting point with the melting point of a hybrid with a nucleic acid containing no mutations. Further, once the melting temperature of a hybrid with a nucleic acid containing no mutations is determined, simple one step detection of mutations by comparing the fluorescence intensity of a sample solution containing an intercalator-labeled probe around the melting temperature with the fluorescence intensity measured with a nucleic acid containing no mutation is possible. For example, the present invention provides means which is clinically effective in making treatment plans for hepatitis C virus, which is classified according to RNA sequence into several types which respond differently to the therapeutic action of interferon.

Further, the method of measuring Tm by fluorescent detection of hybrids according to the present invention is generally more effective than the method based on the hyperchromicity for relatively small amounts of nucleic acids in samples and is also applicable to samples containing only traces of target nucleic acids, which can be amplified to only several ng even by PCR.

In addition, since the present invention permits homogeneous assay without separation of the excessive unhybridized probe, the method of the present invention is simpler and can save labor. Especially, the method of the present invention can be used in actual clinical situations in which a lot of samples have to be examines in a short time and is easy to automate.

What is claimed is:

1. A method of measuring a melting temperature of a nucleic acid, which comprises a step of monitoring the fluorescent intensity of a mixture of a sample and a probe which is labeled with a fluorescent intercalative dye and contains a base sequence complementary to a specific nucleic acid in the sample, while varying the temperature of the mixture; wherein, alteration of the fluorescent intensity with an increase of temperature, will indicate a nucleic acid melting point temperature.

2. The method according to claim 1, wherein the probe labeled with a fluorescent intercalative dye alters its fluorescence by forming a hybrid with the specific nucleic acid so in the sample.

3. The method according to claim 1, wherein the probe labeled with a fluorescent intercalative dye is characterized in that when the probe forms a hybrid with the specific nucleic acid in the sample, the fluorescent intercalative dye intercalates into the hybrid.

4. The method according to claim 2, wherein the hybrid is formed by hybridization of the specific nucleic acid in the sample and the probe.

5. The method according to claim 1, wherein the specific nucleic acid in the sample is amplified by PCR polymerase chain reaction before the step of monitoring the fluorescence intensity.

6. The method according to claim 1, wherein the specific nucleic acid in the sample is amplified by the nucleic acid sequence based amplification NASBA method before the step of monitoring the fluorescence intensity.

7. The method according to claim 1, wherein the step of monitoring the fluorescence intensity is preceded a DNA producing step of producing a double-stranded DNA having a promoter sequence for an RNA polymerase and the nucleic acid sequence of the specific nucleic acid (the specific nucleic acid sequence) downstream from the promoter sequence by using the specific nucleic acid in the sample as a template.

8. The method according to claim 5, wherein the DNA producing step is followed by an RNA producing step of producing a single-stranded RNA having the specific nucleic acid sequence at a constant temperature by adding at least an RNA polymerase, ribonucleoside triphosphates and a probe which is labeled with a fluorescent intercalative dye and is complementary to the resulting RNA to the reaction solution obtained in the DNA producing step.

* * * * *